(12) United States Patent
Matsuki

(10) Patent No.: US 11,158,410 B2
(45) Date of Patent: Oct. 26, 2021

(54) MEDICAL INFORMATION PROCESSING APPARATUS, MEDICAL INFORMATION PROCESSING SYSTEM, MEDICAL INFORMATION PROCESSING METHOD, AND STORAGE MEDIUM

(71) Applicant: CANON KABUSHIKI KAISHA, Tokyo (JP)

(72) Inventor: Naoki Matsuki, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 78 days.

(21) Appl. No.: 15/710,896

(22) Filed: Sep. 21, 2017

(65) Prior Publication Data
US 2018/0089371 A1    Mar. 29, 2018

(30) Foreign Application Priority Data
Sep. 27, 2016  (JP) .............................. JP2016-188755

(51) Int. Cl.
*G16H 50/20* (2018.01)
*G16H 15/00* (2018.01)
(Continued)

(52) U.S. Cl.
CPC ............. *G16H 15/00* (2018.01); *G06F 16/51* (2019.01); *G16H 30/20* (2018.01); *G16H 50/20* (2018.01);
(Continued)

(58) Field of Classification Search
CPC .... G06F 19/321; G06F 17/241; G06F 17/248; G06F 17/2785; G06F 17/28; G06F 40/30;
(Continued)

(56) References Cited

U.S. PATENT DOCUMENTS 5,974,405 A * 10/1999 McGuinness .......... G06N 5/045
706/45
8,438,486 B2 * 5/2013 Waldman .................. G06F 3/14
715/732
(Continued)

FOREIGN PATENT DOCUMENTS

JP  H08186762 A    7/1996
JP  2003223509 A    8/2003
JP  2013252345 A   12/2013

OTHER PUBLICATIONS

Office Action issued in U.S. Appl. No. 15/685,193 dated Dec. 5, 2018.
(Continued)

*Primary Examiner* — Wilson W Tsui
(74) *Attorney, Agent, or Firm* — Rossi, Kimms & McDowell LLP

(57) ABSTRACT

A medical information processing apparatus processes structured document information including a plurality of pieces of partial information obtained by classifying information concerning imaging diagnosis for each predetermined type and relation information indicating a relation between the plurality of pieces of partial information. The medical information processing apparatus includes: a selection unit configured to select partial information and relation information as copy targets from the structured document information which is being displayed; a decision unit configured to decide an arrangement of the partial information in copy information based on the selected partial information and the selected relation information; and a generating unit configured to generate data by converting the selected partial information and the selected relation information based on the decided arrangement.

21 Claims, 17 Drawing Sheets

(51) Int. Cl.
  *G06F 16/51* (2019.01)
  *G16H 30/20* (2018.01)
  *G06F 40/30* (2020.01)
  *G06F 40/10* (2020.01)
  *G06F 40/56* (2020.01)
  *G06F 40/295* (2020.01)
(52) U.S. Cl.
  CPC ............ *G06F 40/10* (2020.01); *G06F 40/295* (2020.01); *G06F 40/30* (2020.01); *G06F 40/56* (2020.01)
(58) Field of Classification Search
  CPC ........ G06F 40/295; G06F 40/10; G06F 40/56; G06F 16/51; G16H 15/00; G16H 10/60; G16H 30/00; G16H 30/20; G16H 30/40; G16H 50/20
  See application file for complete search history.

(56) References Cited

U.S. PATENT DOCUMENTS

| | | | |
|---|---|---|---|
| 9,075,899 B1 | 7/2015 | Reicher | |
| 2003/0063134 A1 | 4/2003 | Lord et al. | |
| 2005/0091603 A1* | 4/2005 | Chen | G06F 9/543 |
| | | | 715/769 |
| 2006/0085435 A1 | 4/2006 | Farn | |
| 2006/0274928 A1* | 12/2006 | Collins | A61B 6/00 |
| | | | 382/132 |
| 2007/0025606 A1* | 2/2007 | Gholap | G06F 16/58 |
| | | | 382/128 |
| 2007/0237377 A1* | 10/2007 | Oosawa | G06F 19/321 |
| | | | 382/128 |
| 2007/0266309 A1* | 11/2007 | Sellman | G06F 17/2229 |
| | | | 715/234 |
| 2011/0002515 A1* | 1/2011 | Futami | G06F 19/321 |
| | | | 382/128 |
| 2011/0199390 A1* | 8/2011 | Iizuka | G06F 19/321 |
| | | | 345/629 |
| 2013/0151954 A1* | 6/2013 | Ierullo | G06F 3/04842 |
| | | | 715/254 |
| 2014/0172458 A1 | 6/2014 | Ueda | |
| 2015/0287389 A1 | 10/2015 | Mese | |
| 2016/0048956 A1* | 2/2016 | Bryan | G06T 7/0012 |
| | | | 382/128 |
| 2016/0364122 A1 | 12/2016 | Shimomura et al. | |
| 2017/0039192 A1* | 2/2017 | Mustafi | G06F 40/56 |
| 2017/0337329 A1* | 11/2017 | Liu | G06F 19/321 |
| 2018/0032679 A1* | 2/2018 | Dandala | G06F 3/0482 |
| 2018/0060491 A1 | 3/2018 | Kikuchi | |
| 2018/0089371 A1 | 3/2018 | Matsuki | |

OTHER PUBLICATIONS

Office Action issued in U.S. Appl. No. 15/685,193 dated May 13, 2019.
Office Action issued in U.S. Appl. No. 15/685,193 dated Dec. 20, 2019.
Office Action issued in U.S. Appl. No. 15/685,193 dated Apr. 15, 2020.
Office Action issued in U.S. Appl. No. 15/685,193 dated Nov. 23, 2020.
Notice of Allowance issued in U.S. Appl. No. 15/685,193 dated Mar. 22, 2021.
Office Action issued in U.S. Appl. No. 15/685,193 dated Sep. 9, 2021.

* cited by examiner

FIG. 4A

| ID | TYPE | CONTENTS | CERTAINTY FACTOR | REQUEST TAG |
|---|---|---|---|---|
| 12345678-001 | REGION |  | | |
| 12345678-002 | FINDING | A TUMOROUS LESION OF ABOUT 25 mm IS RECOGNIZED IN THE LEFT LUNG UPPER LOBE, THE SHAPE OF THE LESION LOOKS IRREGULAR LOBULATED, THE INFILTRATION OF THE LESION INTO THE BRONCHI, ARTERIES, AND VEINS IS RECOGNIZED, THE INSIDE OF THE LESION EXHIBITS A SOFT TISSUE DENSITY, AND THE LESION IS NOT ACCOMPANIED BY OBVIOUS CALCIFICATION. | HIGH | |
| 12345678-003 | DIAGNOSIS | LUNG CANCER CANNOT BE DENIED. | LOW | LUNG CANCER SUSPICION |
| 12345678-004 | REGION |  | | |
| 12345678-005 | FINDING | A TUMOROUS LESION OF ABOUT 20 mm IS RECOGNIZED AT BACK-SIDE PERIPHERY OF RIGHT LUNG S2, HAS A LOBULATED SHAPE WITH ITS SURROUNDING BEING ACCOMPANIED BY CONTRACTION, AND IS PARTIALLY ACCOMPANIED BY CALCIFICATION. | HIGH | |
| 12345678-006 | DIAGNOSIS | MULTIPLE PULMONARY METASTASIS OF COLORECTAL CANCER IS SUSPECTED. | INTERMEDIATE | LUNG CANCER SUSPICION |
| 12345678-007 | DIAGNOSIS | COLORECTAL CANCER IS POSSIBLE. | INTERMEDIATE | |
| ⋮ | ⋮ | ⋮ | ⋮ | ⋮ |

| ENTRY ID1 | ENTRY ID2 | TYPE |
|---|---|---|
| 12345678-001 | 12345678-002 | CORRESPONDENCE RELATION |
| 12345678-002 | 12345678-003 | CAUSE-EFFECT RELATION |
| 12345678-002 | 12345678-006 | CAUSE-EFFECT RELATION |
| 12345678-004 | 12345678-005 | CORRESPONDENCE RELATION |
| 12345678-005 | 12345678-006 | CAUSE-EFFECT RELATION |
| 12345678-005 | 12345678-007 | CAUSE-EFFECT RELATION |
| 12345678-006 | 12345678-007 | ADVERSARIAL RELATION |
| 12345623-004 | 12345678-005 | TIME-SERIES RELATION |
| ... | ... | ... |

FIG. 6A

A TUMOROUS LESION OF ABOUT 26 mm IS RECOGNIZED IN THE LEFT LUNG UPPER LOBE, THE SHAPE OF THE LESION LOOKS IRREGULAR LOBULATED, THE INFILTRATION OF THE LESION INTO THE BRONCHI, ARTERIES, AND VEINS IS RECOGNIZED, THE INSIDE OF THE LESION EXHIBITS A SOFT TISSUE DENSITY, AND THE LESION IS NOT ACCOMPANIED BY OBVIOUS CALCIFICATION.

FIG. 6B

| EVENT | TUMOROUS LESION |
|---|---|
| REGION | LEFT LUNG UPPER LOBE |
| SIZE | ABOUT 26 mm |
| SHAPE | IRREGULAR LOBULATED |
| INFILTRATION | BRONCHI, ARTERIES, AND VEINS |
| DENSITY | SOFT TISSUE DENSITY |
| DENSITY | NOT ACCOMPANIED BY OBVIOUS CALCIFICATION |

F I G. 7B

| DATE AND TIME | TITLE | LESION/EVENT | REGION | SIZE | DENSITY | SHAPE | SURROUNDING | TYPICAL IMAGE |
|---|---|---|---|---|---|---|---|---|
| 2013/06/23 11:52:00 | [TUMOROUS LESION AT BACK-SIDE PERIPHERY OF RIGHT LUNG S2] | TUMOROUS LESION | BACK-SIDE PERIPHERY OF RIGHT LUNG S2 | ABOUT 18 mm | PARTIALLY ACCOMPANIED BY CALCIFICATION | LOBULATED | CONTRACTION |  IMAGE |
| 2013/9/12 15:32:00 | [TUMOROUS LESION AT BACK-SIDE PERIPHERY OF RIGHT LUNG S2] | TUMOROUS LESION | BACK-SIDE PERIPHERY OF RIGHT LUNG S2 | ABOUT 21 mm | PARTIALLY ACCOMPANIED BY CALCIFICATION | LOBULATED | CONTRACTION | 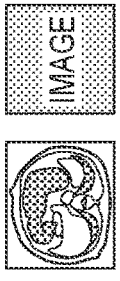 IMAGE |
| 2013/12/25 12:30:00 | [TUMOROUS LESION AT BACK-SIDE PERIPHERY OF RIGHT LUNG S2] | TUMOROUS LESION | BACK-SIDE PERIPHERY OF RIGHT LUNG S2 | ABOUT 23 mm | PARTIALLY ACCOMPANIED BY CALCIFICATION | LOBULATED | CONTRACTION | 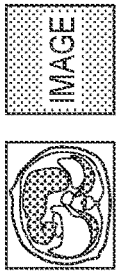 IMAGE |

FIG. 11A

| | 1101 | 1102 | 1103 |
|---|---|---|---|
| ID | Id : 12344592-005 | Id : 12345523-001 | Id : 12345678-001 |
| DATE AND TIME | 2013/06/23 11:52:00 | 2013/9/12 15:32:00 | 2013/12/25 12:30:00 |
| LESION/EVENT | TUMOROUS LESION | TUMOROUS LESION | TUMOROUS LESION |
| REGION | BACK-SIDE PERIPHERY OF RIGHT LUNG S2 | BACK-SIDE PERIPHERY OF RIGHT LUNG S2 | BACK-SIDE PERIPHERY OF RIGHT LUNG S2 |
| SIZE | ABOUT 18 mm | ABOUT 21 mm | ABOUT 23 mm |
| DENSITY | PARTIALLY ACCOMPANIED BY CALCIFICATION | PARTIALLY ACCOMPANIED BY CALCIFICATION | PARTIALLY ACCOMPANIED BY CALCIFICATION |
| SHAPE | LOBULATED | LOBULATED | LOBULATED |
| SURROUNDING | CONTRACTION | CONTRACTION | CONTRACTION |

FIG. 11B

```
       <text>---------------------------------------------------</text>
1104 { <ctime id="12344592-005" />
       <entry id="12344592-005" type="structure"/>

1105 { <ctime id="12345523-001" />
       <entry id="12345523-001" type="structure"/>

1106 { <ctime id="12345678-001" />
       <entry id="12345678-001" type="structure"/>

1107 { <link id="12344592-005,12345523-001,12345678-001">
       <text>---------------------------------------------------</text>
```

F I G. 11C

1108
- 2013/06/23
- [12344592-005]
- LESION/EVENT : TUMOROUS LESION
- REGION : BACK-SIDE PERIPHERY OF RIGHT LUNG S2
- SIZE : ABOUT 18 mm
- DENSITY : PARTIALLY ACCOMPANIED BY CALCIFICATION
- SHAPE : LOBULATED
- SURROUNDING : CONTRACTION

1109
- 2013/09/12
- [12345523-001]
- LESION/EVENT : TUMOROUS LESION
- REGION : BACK-SIDE PERIPHERY OF RIGHT LUNG S2
- SIZE : ABOUT 21 mm
- DENSITY : PARTIALLY ACCOMPANIED BY CALCIFICATION
- SHAPE : LOBULATED
- SURROUNDING : CONTRACTION

1110
- 2013/12/25
- [12345678-001]
- LESION/EVENT : TUMOROUS LESION
- REGION : BACK-SIDE PERIPHERY OF RIGHT LUNG S2
- SIZE : ABOUT 23 mm
- DENSITY : PARTIALLY ACCOMPANIED BY CALCIFICATION
- SHAPE : LOBULATED
- SURROUNDING : CONTRACTION

1111
INCREASES IN SIZE WITH THE LAPSE OF TIME IS RECOGNIZED BETWEEN FINDING 12344592-005, FINDING 12345523-001, AND FINDING 12345678-001. THERE ARE NO CHANGES IN OTHER ATTRIBUTES.

F I G. 12B

```
<text>-----------------------------------------------</text>
<text>[IMAGE FINDING]</text>
1205 {  <entry id="12345678-001" type="plane"/>
        <entry id="12345678-005" type="plane"/>

<text>[IMAGING FINDING]</text>
1206 {  <entry id="12345678-002" type="plane"/>
        <entry id="12345678-008" type="plane"/>

1207 {  <link id="12345678-001,12345678-002,12345678-008"/>
        <link id1="12345678-002"id2="12345678-008"/>
<text>-----------------------------------------------</text>
```

F I G. 12C

```
-----------------------------------------
[IMAGE FINDING]
[001]A TUMOROUS LESION OF ABOUT 26 mm IS RECOGNIZED IN THE
LEFT LUNG UPPER LOBE, THE SHAPE OF THE LESION LOOKS
1208 { IRREGULAR LOBULATED, THE INFILTRATION OF THE LESION INTO
THE BRONCHI, ARTERIES, AND VEINS IS RECOGNIZED, THE INSIDE
OF THE LESION EXHIBITS A SOFT TISSUE DENSITY, AND THE LESION
IS NOT ACCOMPANIED BY OBVIOUS CALCIFICATION.

[IMAGE FINDING]
1209 { [002]LUNG CANCER CANNOT BE DENIED.
[008]MULTIPLE PULMONARY METASTASIS OF COLORECTAL CANCER
IS SUSPECTED.

1210 { DIAGNOSIS 002 AND DIAGNOSIS 008 ARE DERIVED FROM FINDING 001.
DIAGNOSIS 002 CONTRACTS DIAGNOSIS 008.
-----------------------------------------
```

MEDICAL INFORMATION PROCESSING APPARATUS, MEDICAL INFORMATION PROCESSING SYSTEM, MEDICAL INFORMATION PROCESSING METHOD, AND STORAGE MEDIUM

BACKGROUND OF THE INVENTION

Field of the Invention

The present invention relates to a medical information processing apparatus, a medical information processing system, a medical information processing method, and a storage medium.

Description of the Related Art

With recent improvements in the performance of imaging apparatuses that obtain medical images, the information amount of image data obtained by examinations have increased, and the necessity of interpretation doctors having the expert knowledge of imaging diagnosis has increased. The imaging diagnosis result obtained by an interpretation doctor is compiled as an electronic report (interpretation report) and provided to the requesting doctor who has requested an examination. The medical care records made by the requesting doctor are saved as health records for each subject. The imaging diagnosis result obtained by the interpretation doctor is handled as one of the findings on the health record. The requesting doctor transcribes the contents of the interpretation report onto the health record to refer to the contents when making diagnosis.

In recent years, electronic health records have been widely adopted, and techniques for transcribing an interpretation report onto an electronic health record have been proposed. For example, Japanese Patent Laid-Open No. 2003-223509 discloses a technique of collectively copying the ranges in a plurality of regions selected by a doctor.

The arrangement disclosed in Japanese Patent Laid-Open No. 2003-223509, however, cannot copy information indicating the relation between the written contents of a plurality of regions. For this reason, simply arranging and pasting selected contents will lead to the loss of the relation between the respective written contents of the plurality of regions indicated on the original interpretation report.

The present invention has been made in consideration of the above problem, and provides a technique capable of saving document information without any omission.

SUMMARY OF THE INVENTION

According to one aspect of the present invention, there is provided a medical information processing apparatus which processes structured document information including a plurality of pieces of partial information obtained by classifying information concerning imaging diagnosis for each predetermined type and relation information indicating a relation between the plurality of pieces of partial information, the apparatus comprising: a selection unit configured to select partial information and relation information as copy targets from the structured document information which is being displayed; a decision unit configured to decide an arrangement of the partial information in copy information based on the selected partial information and the selected relation information; and a generating unit configured to generate data by converting the selected partial information and the selected relation information based on the decided arrangement.

According to the present invention, document information can be saved without any omission.

Further features of the present invention will become apparent from the following description of exemplary embodiments (with reference to the attached drawings).

BRIEF DESCRIPTION OF THE DRAWINGS

FIGS. 4A and 4B are views each showing an example of how partial information and relation information are stored;

FIGS. 6A and 6B are views showing display examples of entry contents;

FIGS. 7A and 7B are views each exemplarily showing the display format of entries;

FIGS. 11A to 11C are views showing examples of a text generation template and a generated text; and FIGS. 12A to 12C are views showing examples of a text generation template and a generated text.

DESCRIPTION OF THE EMBODIMENTS

An embodiment of the present invention will be exemplarily described in detail below with reference to the accompanying drawings. Note, however, that the constituent elements described in this embodiment are merely exemplary, and the technical scope of the present invention is determined by the scope of the claims, but is not limited to each individual embodiment described below.

A medical information processing apparatus 10 according to this embodiment displays medical document information (for example, an interpretation report) as structured document information to facilitate the understanding of the contents of the medical document information. That is, the medical information processing apparatus 10 displays information concerning imaging diagnosis as structured document information including a plurality of pieces of partial information (to be also referred to as entries hereinafter) classified according to each predetermined type and links (to be also referred to as relation information hereinafter) indicating the relations between the plurality of pieces of partial information. This allows the user to grasp a logical procedure for imaging diagnosis at a glance.

In addition, when partially selecting the contents of an interpretation report and saving the selected information in an electronic health record, the medical information processing apparatus 10 according to this embodiment generates data (complementary data for explaining links as text data) for holding the arrangement of entries in copy data, a display format, and the relations between the entries based on the display state of the partial information (entries) selected as copy targets. This makes it possible to save the information of the interpretation report without any omission.

(Example of Arrangement of Medical Information Processing Apparatus)

Figure 1:
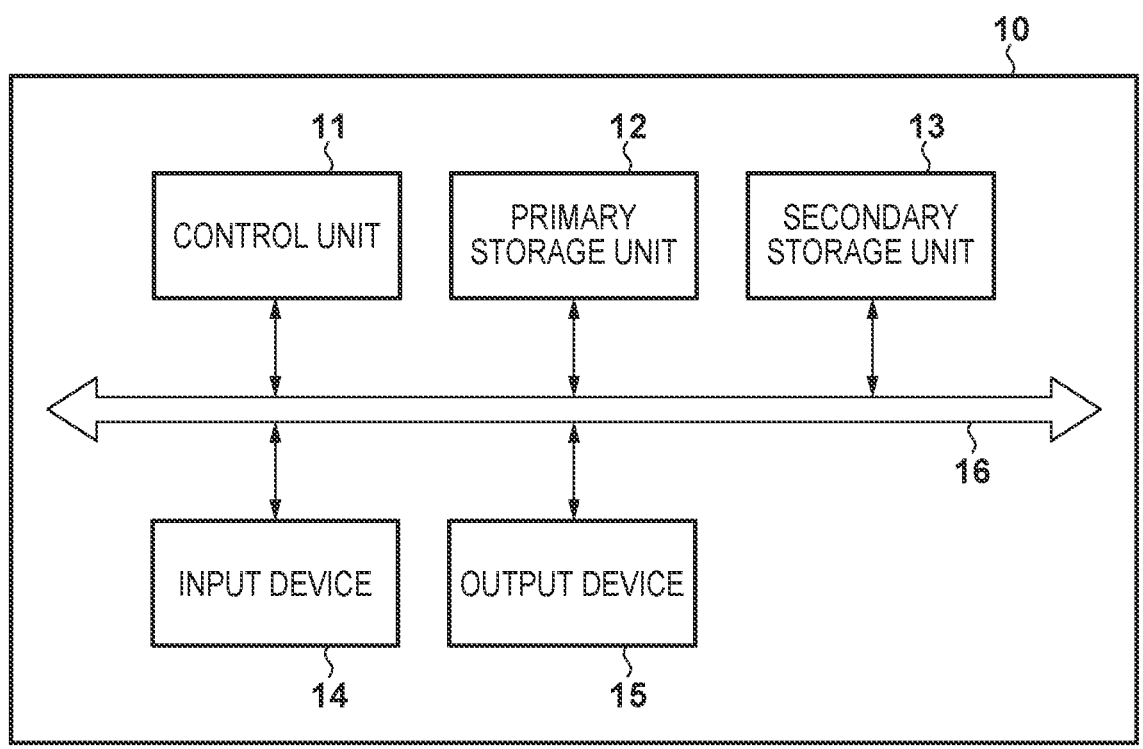
FIG. 1 is a block diagram showing the arrangement of a medical information processing apparatus according to an embodiment.

FIG. 1 is a block diagram showing an example of the arrangement of the medical information processing apparatus 10 according to the embodiment of the present invention. A control unit 11 includes, for example, a CPU (Central Processing Unit), and can comprehensively control processing for a medical document (for example, an interpretation report) in the medical information processing apparatus 10.

A primary storage unit 12 can be implemented by, for example, a storage medium such as a RAM, and temporarily stores various types of information and various types of programs. The primary storage unit 12 can load programs and the like stored in a secondary storage unit 13 and temporarily store them. The secondary storage unit 13 can be implemented by, for example, a storage medium such as a hard disk or flash memory, and stores various types of programs and various types of information. The secondary storage unit 13 can store programs, data, and the like that cannot be stored in the primary storage unit 12. In addition, data and the like that need to be stored for a long time are also stored in the secondary storage unit 13.

An input device 14 (operation unit) includes, for example, a pointing device such as a mouse, a touch panel, and a keyboard, and inputs an instruction from a user (for example, a doctor) to the apparatus.

An output device 15 includes, for example, a monitor such as an LCD and a printer, and outputs various types of information to the user. Note that it is possible to use, for example, a combination of an arbitrary number of monitors as the output device 15.

A system bus 16 controls the flow of data. The control unit 11, the primary storage unit 12, the secondary storage unit 13, the input device 14, and the output device 15 are connected to the system bus 16, and can transmit and receive data to and from each other via the system bus 16.

(Example of Arrangement of Medical Information Processing System)

Figure 2:
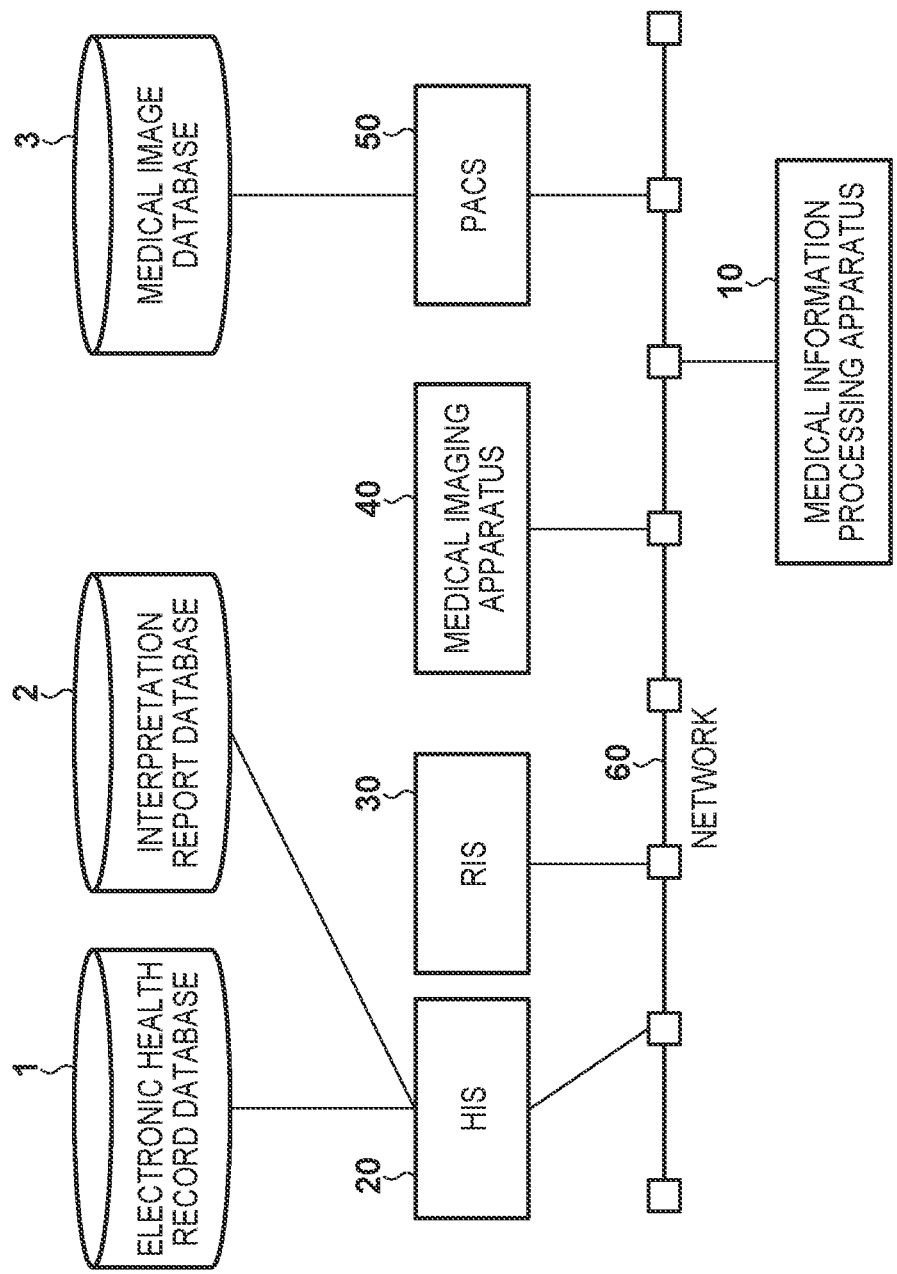
FIG. 2 is a block diagram showing the arrangement of a medical information processing system according to the embodiment.

FIG. 2 is a block diagram showing an example of the arrangement of a medical information processing system including the medical information processing apparatus 10 according to this embodiment. Referring to FIG. 2, an HIS 20 (Hospital Information Systems), an RIS 30 (Radiology Information Systems), a medical imaging apparatus 40, a PACS 50 (Picture Archiving and Communication Systems), and the medical information processing apparatus 10 are connected to a network 60, and are configured to be communicable to each other via the network 60.

The HIS 20 is a comprehensive system including a medical office work/accounting system, medical reservation system, and medical care information system, and can obtain data from an electronic health record database 1 and an interpretation report database 2 by communicating with them. The electronic health record database 1 saves electronic health records in which medical care information concerning subjects is recorded. The interpretation report database 2 saves the interpretation reports generated by interpretation doctors.

The RIS 30 is a system for performing imaging reservation, interpretation management, material inventory management, and the like in a radiology department. The RIS 30 sometimes manages the interpretation report database 2. The medical imaging apparatus 40 includes, for example, a radiation imaging apparatus (or X-ray imaging apparatus), CT apparatus, MRI apparatus, PET apparatus, PET/CT apparatus, SPECT apparatus, ultrasonic imaging diagnosis apparatus, fundus camera (or fundus photography apparatus), and OCT apparatus. The PACS 50 is a system for electronically saving, searching for, and communicating medical images obtained by the medical imaging apparatus 40. The medical information processing apparatus 10 can obtain images from a medical image database 3 by communicating with it via the PACS 50.

Figure 5:
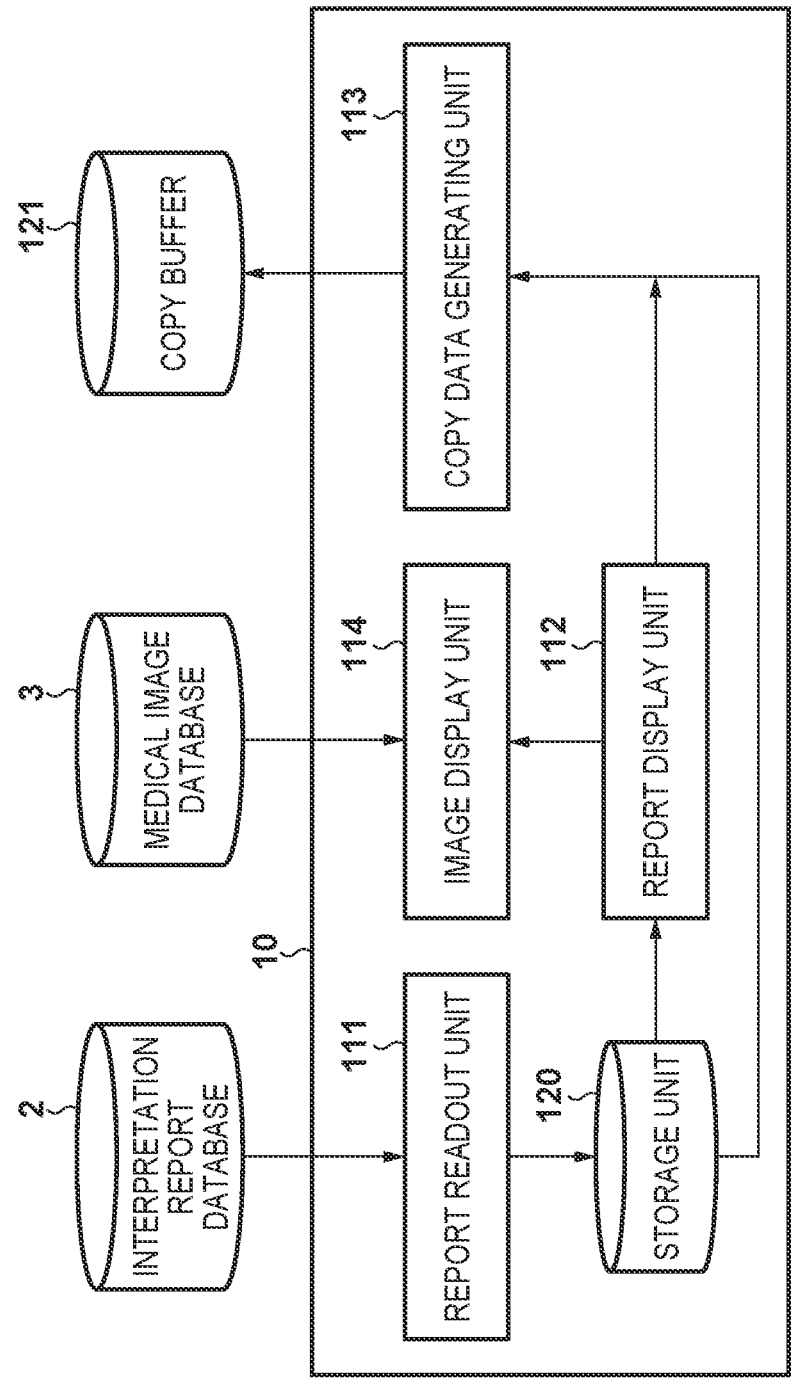
FIG. 5 is a view showing the functional arrangement of the medical information processing apparatus.

The medical information processing apparatus 10 includes various types of functions required to allow the interpretation doctor to browse an image as an interpretation target and generate an interpretation report. The functional arrangement of the medical information processing apparatus 10 will be described later with reference to FIG. 5.

(Arrangement of Interpretation Report)

Figure 3:
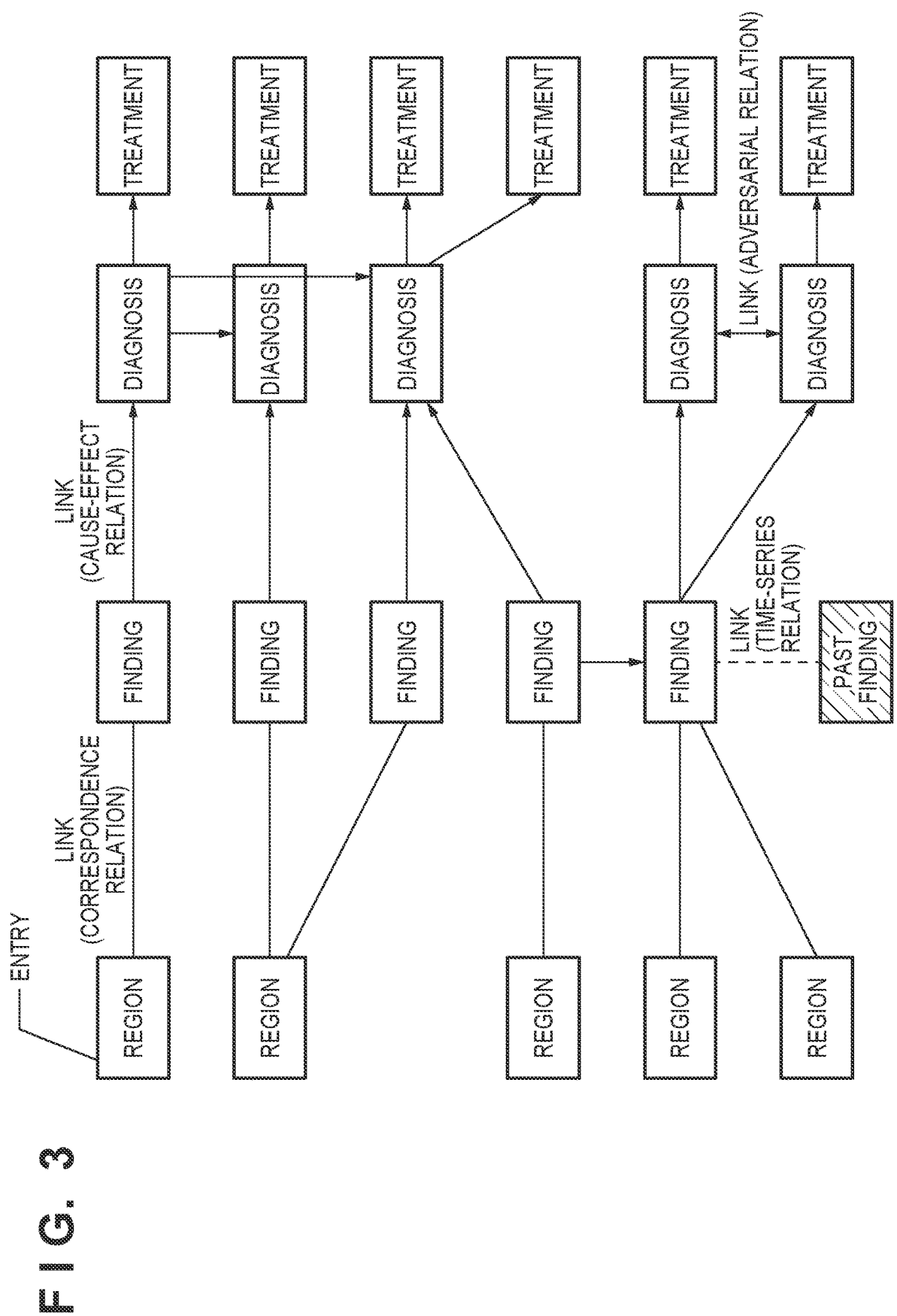
FIG. 3 is a block diagram exemplarily showing a concept of an interpretation report displayed by the medical information processing apparatus.

FIG. 3 exemplarily shows a concept of the interpretation report displayed by the medical information processing apparatus 10 according to this embodiment. The medical information processing apparatus 10 processes structured document information including a plurality of pieces of partial information (entries) obtained by classifying information concerning imaging diagnosis for each predetermined type and relation information (links) indicating the relations between the plurality of pieces of partial information. As shown in FIG. 3, the structured document information displayed by the medical information processing apparatus includes a plurality of pieces of partial information (entries) and relation information (links) representing the relations between the entries.

Partial information (entries) is classified into four types of items, namely a region, finding, diagnosis, and treatment. A document or image information that can specify a region in the body of a subject is input to partial information (region entry) indicating the region. The image information input to a region entry includes, for example, a soft copy of the interpretation target image displayed on the monitor of the output device 15 and address information for accessing the interpretation target image saved in the medical image database 3. At this time, such information may be input to the region entry, together with, for example, a parameter for the image processing to be applied when the user browses the image.

A text explaining one or more lesions is input to a finding entry. A text explaining one or more diseases is input to a diagnosis entry. A text explaining one or more treatments is input to a treatment entry.

Relation information (links) is classified into four types, namely a correspondence relation, cause-effect relation, adversarial relation, and time-series relation, in accordance with the relations between entries. A correspondence relation indicates that two entries are related to each other. A cause-effect relation indicates that one of two entries is a cause, and the other is an effect. An adversarial relation indicates that two entries contradict each other. A time-series relation indicates that two entries have the contents obtained by observing the same target in different periods.

Assume that in the relation information (links) shown in FIG. 3, the lines (solid lines) indicate the correspondence relations, and the single-headed arrows indicate the cause-effect relations. For example, the entry on the starting point side of a single-headed arrow indicates a cause, and the entry on the ending point side of the single-headed arrow indicates an effect. Assume also that the double-headed arrow represents an adversarial relation, and the broken line represents a time-series relation. In order to clarify the time-series relation between entries, for example, display control can be performed for one (past finding) of two entries which indicates a past finding with older time information so as to make it identifiable by changing the display format of the entry (for example, changing the display color or size of an entry frame surrounding partial information).

One entry can have relations with a plurality of other entries. That is, entries can have many-to-many relations via a plurality of pieces of relation information (links). In this embodiment, assume that information concerning various types of interpretation reports in the format shown in FIG. 3 is saved in the interpretation report database 2 in advance while being held in a table holding entry information indicating the contents of each entry and a table holding relation information (links) indicating the mutual relations between the entries.

FIGS. 4A and 4B show examples of how entry information and relation information (links) are stored. An entry table 101 shown in FIG. 4A is a table holding entry information indicating the contents of each entry. A link table 102 shown in FIG. 4B is a table holding relation information indicating the mutual relations between the entries. Entry information and relation information concerning an interpretation report as a processing target are read out from the interpretation report database 2 and held in a storage unit 120. With regard to an interpretation report as a processing target, the storage unit 120 holds identification information for specifying partial information constituting structured document information (interpretation reports and the like), information indicating the types and contents of partial information, and relation information (links) indicating the relations between the partial information.

The entry table 101 shown in FIG. 4A holds identification information (IDs) of entries in an interpretation report, the types and contents of partial information (entries), the certainty factors of the contents, and request items (request tags) corresponding to the partial information (entries). A text or image information that can specify a region in the body of a subject can be input to an entry (region entry) indicating a region type. In the example shown in FIG. 4A, a soft copy of an interpretation target image is input to the entry. Alternatively, address information for accessing an interpretation target image saved in the medical image database 3 can be input as image information.

The pieces of identification information (IDs) of partial information (entries) are generated in combination with the identification information of an interpretation report, which is used to access the interpretation report, so as to allow each entry to be specified in the interpretation report. In addition, it is possible to obtain the identification information of an interpretation report including an entry from the identification information (ID) of the entry. For example, "12345678" of "12345678-001" which is the identification information (ID) of an entry is the identification information of the interpretation report which is used to access the interpretation report. A target interpretation report can be specified by the identification information of the interpretation report. Of the identification information (ID) of an entry, "001" is information for specifying the display position of an entry in the interpretation report which is specified by the identification information of the interpretation report.

The entry table 101 saves display data concerning display (natural language text display) expressed by a plain text and display (structured display) with attribute information concerning imaging diagnosis being associated with information indicating values corresponding to the attribute information. When entry information is read out from the interpretation report database 2, display data is also read out and held in the storage unit 120. The control unit 11 can selectively obtain display data (display data for natural language text display and display data for structured display) based on input information from the input device 14. When displayed partial information (entry) is selected with the input device 14, the control unit 11 can determine, by referring to the storage unit 120, whether the display state of the displayed entry is a natural language text display state or structured display state. Note that only reports in natural language text display form may be saved as data read out from the interpretation report database 2 and stored in the storage unit 120, and the reports may be converted into those in a structured format when being displayed on the medical information processing apparatus 10.

The link table 102 shown in FIG. 4B saves the identification information (IDs) of two pieces of partial information (entries) in association with information indicating the type of relation information (link) set between them. For example, referring to FIG. 4B, "correspondence relation" is set as information indicating a type between "12345678-001" which is the identification information (ID1) of an entry and "12345678-002" which is the identification information (ID2) of an entry. Regarding an interpretation report as a processing target, information like that shown in FIG. 4B is read out from the interpretation report database 2 and held in the storage unit 120.

(Functional Block)

When executing programs, for example, the control unit 11 uses the primary storage unit 12 as a work area, loads and executes various types of programs stored in the secondary storage unit 13 to implement the functions of the respective constituent elements. The control unit 11 includes a functional arrangement like that shown in FIG. 5 by, for example, implementing the programs stored in the secondary storage unit 13.

In the medical information processing apparatus 10 according to this embodiment, a report readout unit 111 reads out a plurality of pieces of partial information (entries) and relation information indicating the relations between the plurality of pieces of partial information, with regard to an interpretation report as a processing target, from the interpretation report database 2. The report readout unit 111 temporarily saves the plurality of pieces of readout partial information (entries) and the readout relation information in the storage unit 120 (primary storage unit 12 or secondary storage unit 13).

The report readout unit 111 can specify an interpretation report as a processing target based on the identification information of the interpretation report (for example, "12345678" shown in FIGS. 4A and 4B). The report readout unit 111 then obtains entry information including the identification information of the interpretation report and the relation information from the interpretation report database 2, and saves them in the storage unit 120. In addition, the report readout unit 111 obtains time information including date/time information corresponding to each partial information (entry) from the interpretation report database 2 and saves it in the storage unit 120.

A report display unit 112 displays the contents of the plurality of pieces of partial information (entries) and relation information (links) saved in the storage unit 120 on the monitor of the output device 15. The report display unit 112 can control the display format of partial information (entries). The report display unit 112 can switch between "natural language text display" and "structured display" by using, for example, the GUI (Graphical User Interface) to be described later with reference to FIG. 8. When the user selects "natural language text display" by using the GUI, the report display unit 112 can perform display control so as to display the contents of partial information (entries) in natural language text form. When the user selects "structured display" by using the GUI, the report display unit 112 can perform display control so as to display the contents of the partial information (entries) in association with attribute information concerning imaging diagnosis and information indicating values corresponding to the attribute information.

FIGS. 6A and 6B are views showing display examples of partial information (entries). FIG. 6A shows a display example of partial information (entries) when "natural language text display" is selected. FIG. 6B shows a display example of partial information (entries) when "structured display" is selected. Referring to FIG. 6B, attribute information includes "event", "region", "size", "shape", "infiltration", and "density", and values corresponding to the attribute information include "tumorous lesion", "left lung upper lobe", "about 26 mm", "irregular lobulated", "bronchi, arteries, and veins", "soft tissue density", and "not accompanied by obvious calcification". The attribute information and the values corresponding to the attribute information are displayed in association with each other.

The report display unit 112 can also control the display format of a plurality of pieces of partial information (entries). The report display unit 112 can switch between presenting only "logical relation display" by using the GUI described with reference to FIG. 8 and concurrently presenting "logical relation display" and "time-series relation display". Note that "logical relation display" is the display format of relation information (links), which displays the correspondence relations, cause-effect relations, and adversarial relations between a plurality of pieces of partial information (entries) by using lines (solid lines) and arrows (single- and double-headed arrows). Note that "time-series relation display" is a display format that displays the time-series relations between a plurality of pieces of partial information (entries) in table form.

Figure 7A:

FIGS. 7A and 7B are views exemplarily showing the display formats of a plurality of pieces of partial information (entries). FIG. 7A exemplarily shows "logical relation display", with the line (solid line) links being set between entries exhibiting correspondence relations, the single-headed arrow links being set between entries exhibiting cause-effect relations, and the double-headed arrow link being set between entries exhibiting an adversarial relation. FIG. 7B exemplarily shows "time-series relation display". In this case, the report display unit 112 obtains time information corresponding to each entry from the storage unit 120, and displays the time-series relations between the entries based on the obtained time information.

A copy data generating unit 113 generates copy data to be pasted to another system based on the method to be described later with reference to FIG. 10. The copy data generating unit 113 saves the generated copy data in a copy buffer 121 (copy information storage unit) prepared on the primary storage unit 12. For example, when partial information and relation information (link) are selected as copy targets from displayed structured document information (interpretation report or the like) based on input information from the input device 14, the copy data generating unit 113 decides the arrangement of the partial information in copy information based on the selected partial information and relation information. In this case, the copy data generating unit 113 determines a data format that allows processing at the paste destination at which the selected partial information and relation information are pasted. The copy data generating unit 113 then generates data by converting the format of the selected partial information and relation information (link) based on the determination result.

An image display unit 114 reads out a display target image from the medical image database 3 via the PACS 50, and displays the image on the monitor of the output device 15. In the images saved in the medical image database 3, partial information (partial entries) indicating regions on interpretation reports and corresponding identification information (IDs) are set to allow the image display unit 114 to acquire an image of the region to be displayed as a display target based on identification information (ID) and display the image on the monitor.

Note that some or all of the functions of the constituent elements of the medical information processing apparatus 10 may be implemented by dedicated circuits. In addition, some of the functions of the constituent elements provided by the control unit 11 by executing programs may be implemented by using a cloud computer.

(Example of User Interface)

Figure 8:
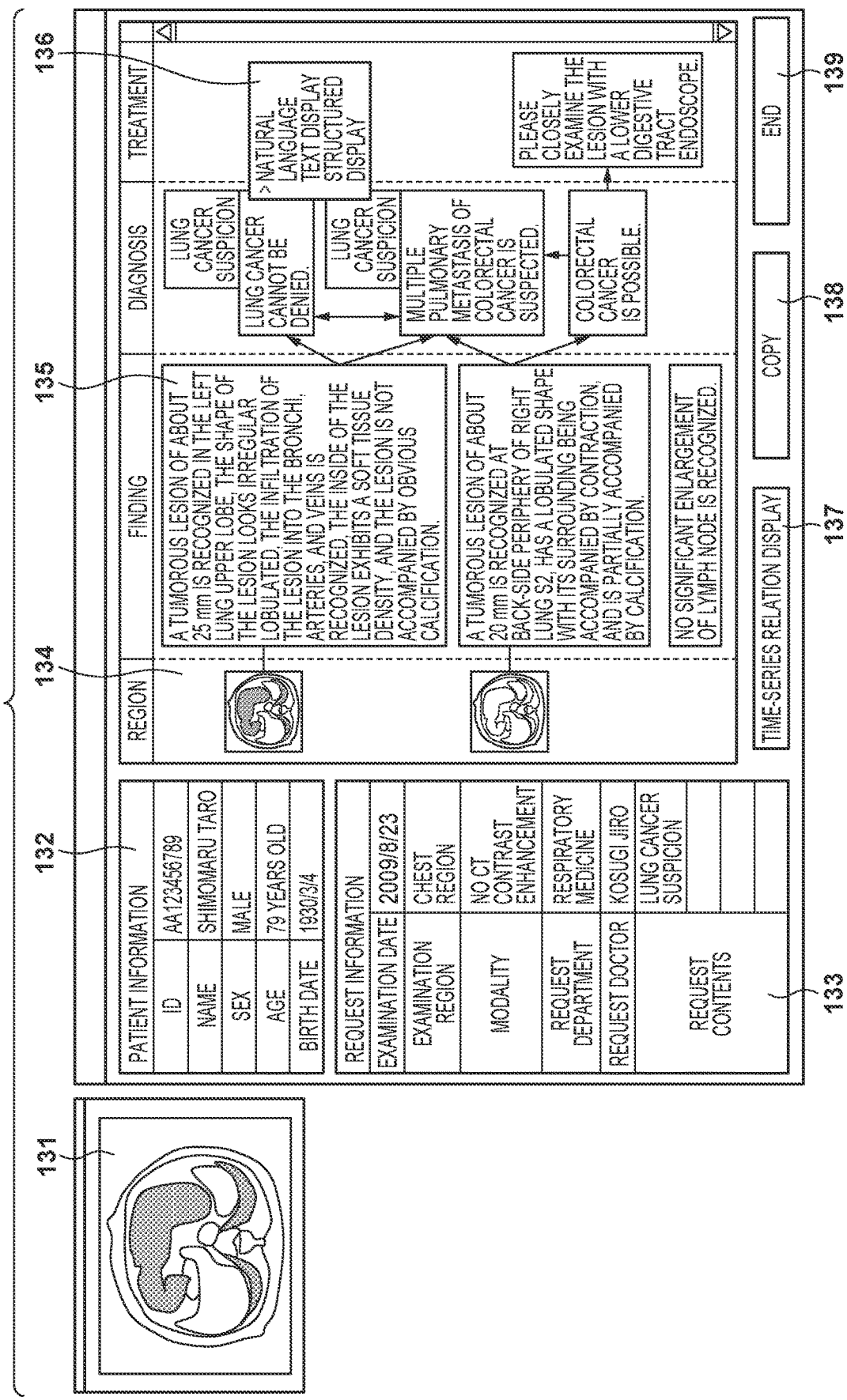
FIG. 8 is a view exemplarily showing a GUI for the medical information processing apparatus.

FIG. 8 exemplarily shows a GUI for the medical information processing apparatus 10 according to this embodiment. The image display unit 114 performs display control to display, on an image browsing window 131, the image (medical image) read out from the medical image database 3 via the PACS 50.

In addition, the control unit 11 of the medical information processing apparatus 10 performs display control to display, in a subject information display area 132, information concerning the subject (subject information) as the object of the image as an interpretation target acquired from the electronic health record database 1 via the HIS 20. The information concerning the subject includes, for example, a subject ID, name, age, and past medical history.

The control unit 11 performs display control to display, in a request information display area 133, the department information of a request source, a requested examination, and request contents from a requesting doctor. In this embodiment, request contents are classified into individual items in advance, and configured to be selectable as request tags for each item. A request tag is associated with an entry. When the request tag is selected via the input device 14, the control unit 11 can perform display control to, for example, highlight an entry frame 135 of an entry corresponding to the selected request tag.

In a report display area 134, information concerning imaging diagnosis is classified according to predetermined types (for example, the areas of a region, finding, diagnosis, and treatment). The report display unit 112 performs display control to display, in each area, a display frame (entry frame 135) for displaying the contents of corresponding partial information (entry). A display frame (entry frame 135) is associated with one piece of partial information (entry). Based on the information stored in the storage unit 120, the report display unit 112 performs display control to display, in the report display area 134, the contents of partial information (entry) associated with each display frame (entry frame) and relation information (link) between partial information (entries). Each display frame (entry frame) is configured to be selectable via the input device 14. A plurality of display frames (entry frames) can be collectively selected. Note that the display frames (entry frames) of a plurality of pieces of partial information (entries) displayed by time-series display can also be collectively selected in the same manner.

When the user selects (by, for example, performing a first operation (double-clicking)) the entry frame of partial information (region entry) indicating a region via the input device 14, the image display unit 114 can obtain an image (medical image) corresponding to the selected region entry from the medical image database 3 via the PACS 50, and perform display control to display the obtained image on the image browsing window 131. The image display unit 114 can switch the image to be displayed on the image browsing window 131 by switching the selection of the display frame (entry frame) of partial information (region entry) indicating a region to the selection of another display frame (entry frame).

When the user selects (by, for example, performing a second operation (right clicking)) a display frame (entry frame) via the input device 14, the report display unit 112 can perform display control to display a display switching menu 136 of entry contents. The display switching menu 136 displays "natural language text display" and "structured display" as items. Each menu item is exclusive, so that when one of the items is selected, the other item is set in a non-selective state. For example, when the user selects "natural language text display" in the display of the display switching menu 136, the report display unit 112 performs display control to display the contents of partial information (entry) in natural language text form, as shown in FIG. 6A, which shows the contents of the entry. In contrast to this, when the user selects "structured display", the report display unit 112 performs display control to display the contents of the entry, with attribute information concerning imaging diagnosis being in association with information indicating values corresponding to the attribute information, as shown in FIG. 6B. Note that this embodiment is configured to allow switching between the display methods for each entry frame. However, it is also possible to display a menu for collectively selecting a plurality of entry frames and collectively switching between the display methods.

A time-series display button 137 is a toggle button, which is turned on and off to make the report display unit 112 switch between the contents to be displayed in the report display area 134. When the time-series display button 137 is OFF, the report display unit 112 performs display control to display the logical relations between the entries included in an interpretation report as shown in FIG. 7A. When the time-series display button 137 is ON, the report display unit 112 performs display control to display the time-series relations between the selected entries as shown in FIG. 7B, in addition to the above logical relations.

When the user presses a copy button 138, the copy data generating unit 113 executes processing to generate copy data in accordance with the contents of partial information (entry) selected via the input device 14 and the display state. When the user pressed an end button 139, the control unit 11 performs display control to close the GUI shown in FIG. 8.

When the copy data generating unit 113 selects partial information and relation information as copy targets from displayed structured document information based on an input from the input device 14, the copy data generating unit 113 decides the arrangement of the partial information in the copy information based on the selected partial information and relation information. In this case, the copy data generating unit 113 determines a data format (for example, structured data, graphic data, or text data) that allows processing at the paste destination at which the selected partial information and relation information (link) are pasted based on input information from the input device 14. The copy data generating unit 113 then generates data by converting the format of the selected partial information and relation information based on the determination result.

Upon determining, based on the determination result, that text data is compatible at the paste destination, the copy data generating unit 113 generates a template (text generation template) for generating text data from the selected partial information and relation information (link). That is, in order to generate copy data, the copy data generating unit 113 generates a text generation template for instructing how text data is generated from the contents of partial information (entry) and relation information stored in the storage unit 120. This text generation template is generated in the processing in step S1008 shown in FIG. 10 to be described later.

(Text Generation Template)

Figure 9:
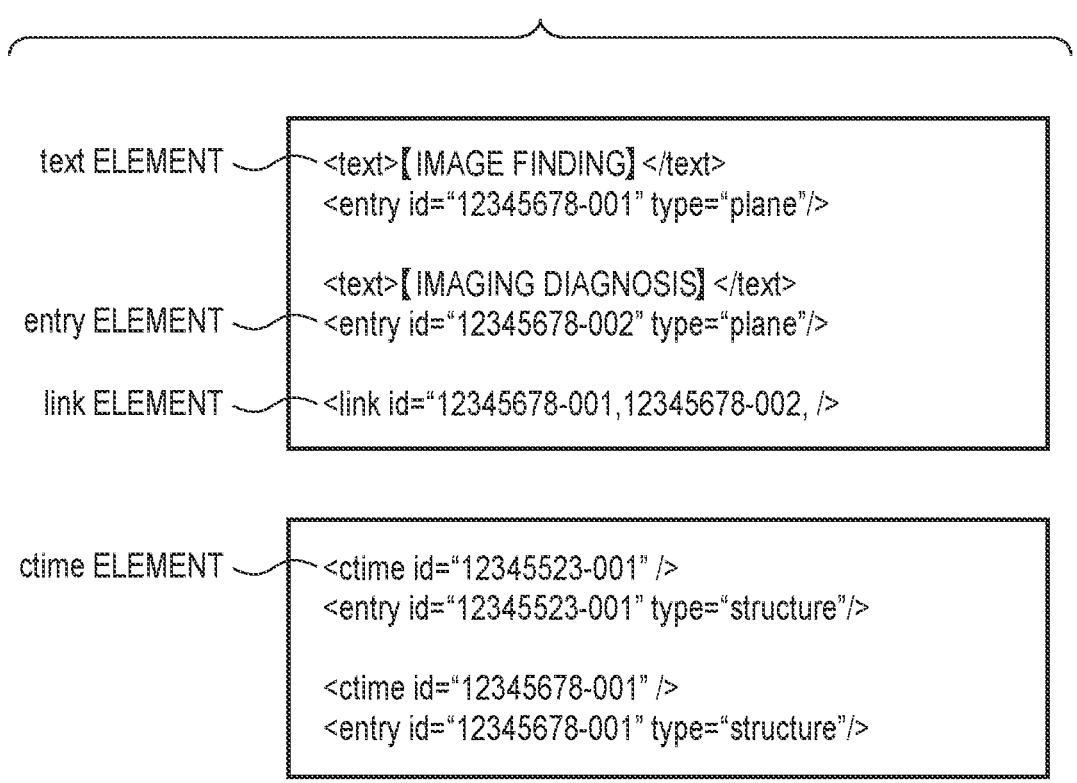
FIG. 9 is a view exemplarily showing a text generation template.

FIG. 9 exemplarily shows a text generation template. A text generation template includes, for example, the tags of "entry" element, "ctime" element, "link" element, and "text" element, which are generated in the XML format. Note that the description format of each element in a text generation template is not limited to the XML format. For example, the HTML format or the like can be used. The copy data generating unit 113 generates a text generation template by obtaining selected partial information and relation information from the storage unit 120.

Note that "entry" element indicates partial information (entry), identification information (ID) for identifying each entry is set to "entry id", and information describing a display format is set to "type". For example, in natural language text display, "plane" is set, wherein in structured display, "structure" is set. In conversion to text data, the contents of partial information (entry) is expanded following a character string representing the identification information (ID) of the entry. That is, the contents of the partial information (entry) specified by the identification information (ID) of the entry are read out from the storage unit 120 and are described according to the set display format.

When "type"="plane" is set as a display format, the contents of an entry are expanded (described) as a plain text to generate the contents of the entry in natural language text display form like that shown in FIG. 6A. When "type"="structure" is set as a display format, the contents of an entry are expanded (described) as a combination of attribute information concerning imaging diagnosis and information indicating values corresponding to the attribute information, thereby generating the contents of the entry in structured display form like that shown in FIG. 6B.

Note that "ctime" element represents the generation date/time of the data of an entry, and the identification information (ID) of the corresponding entry is set to "ctime id". When converting the data of the entry into text data, the copy data generating unit 113 specifies an interpretation report based on the identification information of the interpretation report ("12345678") included in the identification information (for example, "12345678-001") of the designated entry. The copy data generating unit 113 then obtains, from the storage unit 120, information indicating the date and time when a medical image corresponding to the specified interpretation report was obtained, and expands (describes) the information indicating the obtained date and time as a character string.

When partial information and relation information (link) selected as copy targets include relation information indicating the relation between predetermined partial information (entries), the copy data generating unit 113 sets, in a text generation template, information ("link" element) for generating complementary data for explaining the relation information as text data. The types of predetermined relation information include, for example, a cause-effect relation, adversarial relation, and time-series relation. Note that the type of relation information for which complementary data is to be generated is not limited to the above relations and can be arbitrarily set.

Note that "link" element (link element) indicates the setting of a link between a plurality of pieces of partial information (entries) associated with each other, and the pieces of identification information (IDs) of the plurality of pieces of partial information (entries) associated with each other are set with comma delimiters in "link id". Based on the setting of "link" element (link element), when converting to text data, the copy data generating unit 113 can expand (describe) the contents of the identification information (IDs) of designated partial information (entries) and relation information (link) between the partial information (entries) as complementary data (character string) for explaining the contents as text data.

When, for example, relation information (link) indicating a time-series relation is set as the relation between entries in copy source data, the copy data generating unit 113 obtains the contents information between a plurality of entries set in a "link" element 1107 (link element) from the copy buffer 121. The copy data generating unit 113 compares, for example, contents information concerning finding entries. When the pieces of contents information have changed with the lapse of time, the copy data generating unit 113 can generate complementary data (character string) for explaining the relation information (link) as text data, like, for example, "the size of the region has changed with the lapse of time", and add the generated data to text data.

In addition, when relation information (link) indicating a cause-effect relation is set from one entry (for example, finding entry 001) to a plurality of entries (for example, diagnosis entries 002 and 008) in copy source data, the copy data generating unit 113 can expand (describe) the relation information as a character string explaining the contents of the relation information (link) like, for example, "diagnosis 002 and diagnosis 008 are derived from finding 001".

Alternatively, when relation information (link) indicating an adversarial relation is included between a plurality of entries (for example, diagnosis entries 002 and 008) in copy source data, the copy data generating unit 113 can expand (describe) the relation information as a character string explaining the contents of the relation information (link) like, for example, "diagnosis 002 contradicts diagnosis 008".

In "text" element (text element), an arbitrary text as the title of the element to be displayed, for example, "image finding" or "imaging diagnosis", can be described. In converting to text data, the text of the element is expanded (described) without any change.

Note that the constituent elements of the text generation template described with reference to FIG. 9 are an example, and other elements may be prepared. For example, an element to be expanded as an address for accessing partial information (entry) may be prepared. Alternatively, when the contents of partial information (entry) are structured/displayed, each attribute may be configured to be individually designated.

(Copy Data Generation Processing)

Figure 10:
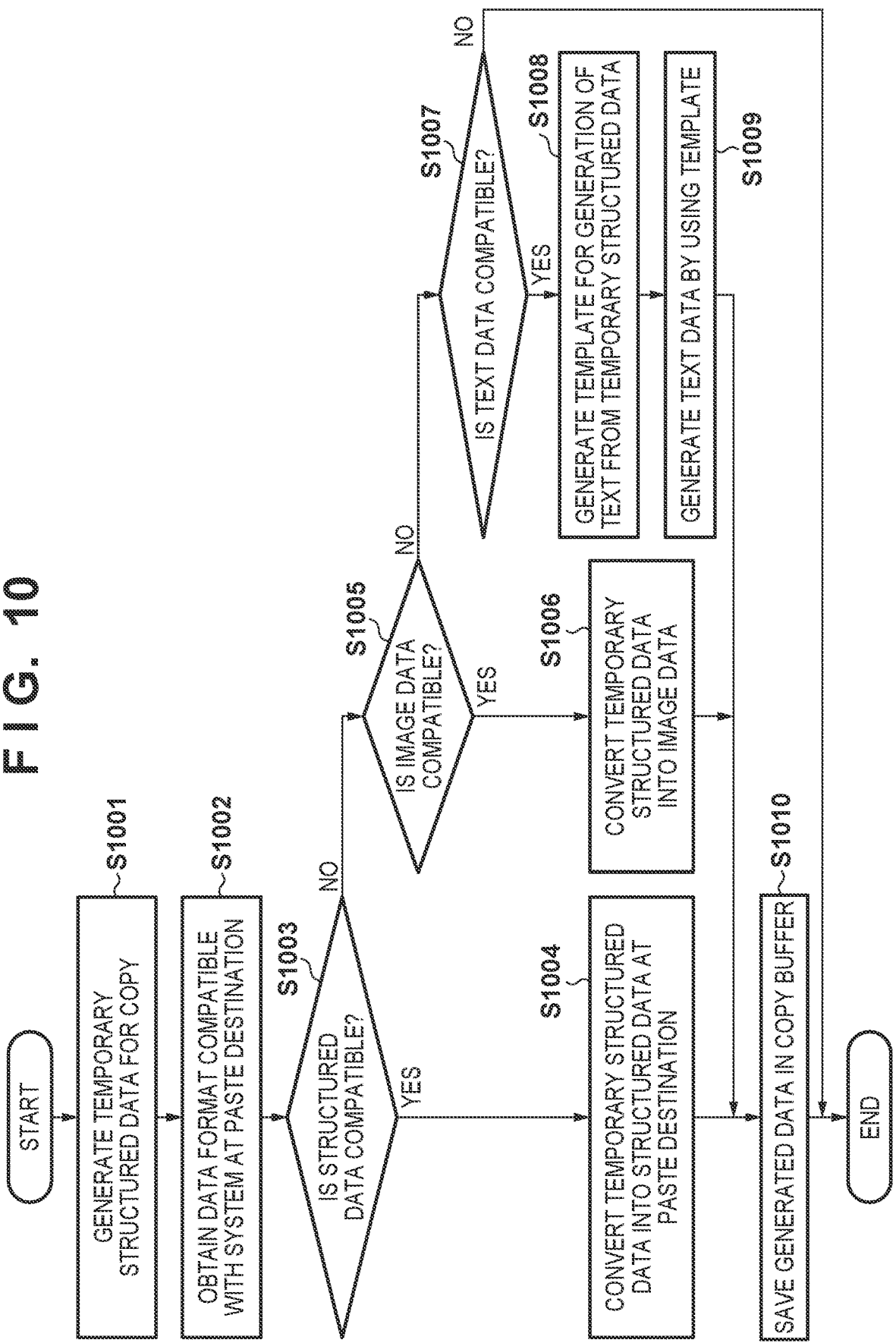
FIG. 10 is a flowchart showing a procedure for copy data generation processing.

FIG. 10 is a flowchart showing a procedure for copy data generation processing executed by the copy data generating unit 113. In step S1001, based on an input from the input device 14, the copy data generating unit 113 selects partial information and relation information (link) as copy targets from displayed structured document information (interpretation report). The copy data generating unit 113 generates the data of the partial information and relation information as the copy targets as temporary structured copy data (to be also referred to as temporary structured data hereinafter). On the GUI shown in FIG. 8, the copy data generating unit 113 obtains information concerning the partial information (entry) and information concerning relation information (link) (link information indicating a link type) selected by the user via the input device 14 from the storage unit 120, and generates temporary structured data. The copy data generating unit 113 saves information indicating the display state of the contents of the selected partial information (entry) in the copy buffer 121 in combination with the temporary structured data. The copy data generating unit 113 can decide the arrangement of the partial information in copy information based on the selected partial information and relation information.

In step S1002, the copy data generating unit 113 decides a data format that allows processing at the paste destination at which the selected partial information and relation information (link) are pasted. The copy data generating unit 113 obtains a data format that is compatible with a system at the paste destination. A compatible data format is, for example, any one of a structured data format, image data format, and text data format or a combination of them. The copy data generating unit 113 obtains the information of a compatible data format by inquiring of the system at the paste destination. Note that the medical information processing apparatus 10 may be provided with an API (Application Program Interface) to allow the system at the paste destination to designate a compatible data format. Note that a compatible data format is not limited to any of a structured data format, image data format, and text data format or a combination of them, and another data format can also be used.

The copy data generating unit 113 then generates data by converting the format of the selected partial information and relation information (link) based on the determination results obtained in steps S1003, S1005, and S1007. In step S1003, first of all, the copy data generating unit 113 determines whether the system at the paste destination is compatible with structured data. If the system is compatible with structured data (YES in step S1003), the process advances to step S1004. Upon determining in step S1003 that structured data is compatible at the paste destination, the copy data generating unit 113 generates data by converting the selected partial information and relation information into structured data that can be processed at the paste destination.

If the copy data generating unit 113 determines in step S1003 that the structured data is not compatible (NO in step S1003), the process advances to step S1005.

In step S1005, the copy data generating unit 113 determines whether the system at the paste destination is compatible with image data. If the system is compatible with image data (YES in step S1005), the process advances to step S1006. Upon determining in step S1005 that image data is compatible at the paste destination, the copy data generating unit 113 generates data by converting the selected partial information and relation information (link) into image data that is compatible at the paste destination. The copy data generating unit 113 renders the selected temporary structured data (partial information and relation information (link)) into image data to generate data converted into an image format that is compatible with the system at the paste destination.

If the copy data generating unit 113 determines in step S1005 that image data is not compatible (NO in step S1005), the process advances to step S1007. The copy data generating unit 113 determines in step S1007 whether text data is compatible with the system at the paste destination. If the copy data generating unit 113 determines in step S1007 that text data is not compatible (NO in step S1007), the processing is terminated. If the copy data generating unit 113 determines that text data is compatible (YES in step S1007), the process advances to step S1008.

Upon determining in step S1007 that text data is compatible at the paste destination, the copy data generating unit 113 generates a template (text generation template) for generating text data from the selected partial information and relation information (link). That is, the copy data generating unit 113 generates a text generation template for generating copy text data based on the temporary structured data generated in step S1001. The copy data generating unit 113 can use, for example, the arrangement described above with reference to FIG. 9 as the arrangement of the text generation template.

The copy data generating unit 113 generates "entry" element corresponding to all the partial information (entries) included in the temporary structured data within the text generation template, and sets the identification information (ID) of the corresponding entry to "entry id". When the display state of each partial information (entry) is natural language text display, the copy data generating unit 113 sets "plane" to "type". When the display state of each partial information (entry) is structured display, the copy data generating unit 113 sets "structure" to "type".

The copy data generating unit 113 then lays out the partial information (entry) in the text generation template based on the partial information (entry) and relation information (link) included in the temporary structured data. That is, the copy data generating unit 113 decides the arrangement of the partial information (entry) in the text generation template based on the partial information (entry) and relation information obtained from the storage unit 120. In addition, the copy data generating unit 113 can select the display format of the partial information in the text generation template based on the display state of the partial information (entry) included in the temporary structured data.

When link information indicating a link type indicates a time-series relation, the copy data generating unit 113 generates "ctime" element in the text generation template, and describes the identification information (ID) of the partial information (entry) in "id" attribute (entry id). In the arrangement generated by the copy data generating unit 113, "ctime" element is arranged before "entry" element, and the contents of information concerning the date and time and partial information (entries) are alternately arranged on the text generation template.

In addition, the copy data generating unit 113 generates "link" element (link element) in the text generation template. In "link id", the pieces of identification information (IDs) of a plurality of pieces of partial information (entries) associated with each other are set.

FIGS. 11A to 11C are views respectively showing temporary structured data when the link information between entries indicates a time-series relation, an example of the arrangement of the text generation template generated based on the temporary structured data, and an example of the text data generated from the text generation template.

FIG. 11A exemplarily shows the temporary structured data when the link information between the entries indicates a time-series relation. In the temporary structured data in FIG. 11A, three structured/displayed entries 1101, 1102, and 1103 are displayed in a time-series relation. The identification information (ID) of the entry 1101 is "12344592-005", the identification information (ID) of the entry 1102 is "12345523-001", and the identification information (ID) of the entry 1103 is "12345678-001".

Based on input information from the input device 14, partial information and relation information (link) (temporary structured data) are selected as copy targets from the structured document information (interpretation report or the like) displayed as shown in FIG. 8. When partial information and relation information (link) are selected as copy targets, the copy data generating unit 113 obtains the pieces of identification information (IDs) of partial information (entries) as processing targets are obtained from the storage unit 120. In addition, the copy data generating unit 113 obtains information indicating the types and contents of the selected partial information (entries) from the storage unit 120. Furthermore, the copy data generating unit 113 obtains link information concerning the selected relation information (link) from the storage unit 120 based on the identification information of the partial information (entries). The copy data generating unit 113 obtains link information indicating the relation (a time-series relation in the example shown in FIG. 11A) between the three pieces of partial information (entries) in the temporary structured data from the storage unit 120. The copy data generating unit 113 generates a template (text generation template) for generating text data from the selected partial information and relation information (link).

FIG. 11B is a view showing an example of the arrangement of a text generation template generated based on selected partial information and relation information (link). Elements 1104 to 1106 corresponding to the entries 1101 to 1103 are arranged in the text generation template. For example, the element 1104 is an element corresponding to the entry 1101. The element 1104 has "ctime" element and "entry" element. Because link information indicates a time-series relation, "ctime" element for indicating date/time information is set. Identification information ("12344592-005") for identifying the entry 1101 is set to "entry id" in "entry" element, and information describing a display format is set to "type". In the examples shown in FIGS. 11A to 11C, because structured display is adopted, "structure" is set. The same applies to the elements 1105 and 1106.

The "link" element 1107 (link element) is set at the end of the text generation template. The identification information of three entries associated with each other is set with comma delimiters at "link id" in the "link" element 1107 (link element). When the partial information and relation information (link) selected as copy targets include relation information indicating the relation (for example, a time-series relation) between predetermined partial information (entries), the copy data generating unit 113 sets information ("link" element) for generating complementary data for explaining the relation information as text data in the text generation template.

FIG. 11C is a view showing an example of the text data generated from the text generation template. A text portion 1108 is the text portion generated by expanding (describing) the element 1104 of the text generation template. The text portion 1108 has a character string representing date/time information, a character string representing the identification information of the entry, and a character string in structured display form, as a character string indicating the contents of the entry, which has a combination of attribute information concerning imaging diagnosis and information indicating values corresponding to the attribute information.

A text portion 1109 is the text portion generated by expanding the element 1105 of the text generation template. A text portion 1110 is the text portion generated by expanding the element 1106 of the text generation template.

A text portion 1111 is the text portion of the complementary data generated by expanding the "link" element 1107 (link element) of the text generation template. The copy data generating unit 113 expands the "link" element 1107 (link element) to generate complementary data for explaining relation information based on a change in the contents information of the entry (partial information). When relation information (link) indicating a time-series relation is set as the relation between the entries, the copy data generating unit 113 obtains a change in the contents information between a plurality of entries which are set in the "link" element 1107 (link element) from the copy buffer 121. For example, the copy data generating unit 113 obtains a finding indicating a change in the size of a region (18 mm→21 mm→23 mm), that is, an increase in the size of the region, as a change in contents information, and a finding indicating no change in attributes other than the size of the region. The copy data generating unit 113 generates complementary data for explaining relation information (link) as text data based on the change in contents information. The copy data generating unit 113 converts the selected partial information into text data by using the text generation template. The copy data generating unit 113 also adds the complementary data generated by using the text generation template to the text data.

In contrast, when the relation information (link) between the entries does not indicate a time-series relation (indicates a logical relation), the copy data generating unit 113 collectively arranges the respective entries (entry elements) in the text generation template for each partial information (entry) type. The copy data generating unit 113 also generates "text" element as a character string representing an entry type and arranges it as a title. In addition, for a structure in which relation information (links) is set from one entry to a plurality of entries, the copy data generating unit 113 generates "link" element and sets the pieces of identification information (IDs) of all the pieces of partial information (entries). Furthermore, when relation information (link) indicating an adversarial relation is set between a plurality of entries, the copy data generating unit 113 generates "link" element and sets the pieces of identification information (IDs) of partial information (entries) in the same manner as described above. That is, when partial information and relation information (links) selected as copy targets include relation information (link) indicating a predetermined relation (for example, a cause-effect relation or adversarial relation) between pieces of partial information (entries), the copy data generating unit 113 sets, in the text generation template, information ("link" element) for generating complementary data for explaining the relation information (link) as text data.

Figure 12A:
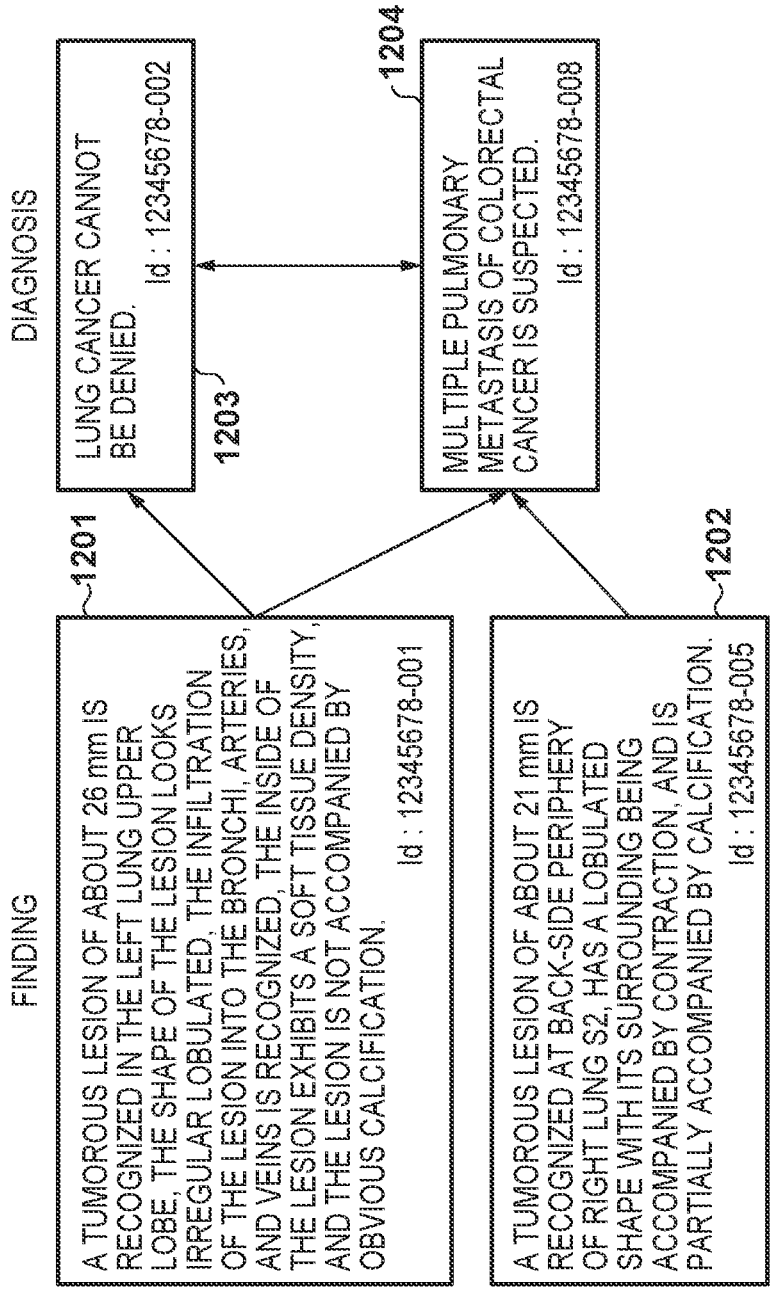

FIGS. 12A to 12C are views respectively showing temporary structured data when the relation information (link) between entries is not a time-series relation, an example of the arrangement of the text generation template generated based on the temporary structured data, and an example of the text generated from the text generation template. FIG. 12A exemplarily shows a temporary structured data when the relation information (link) between entries is not a time-series relation (is a logical relation). The temporary structured data includes two entries 1201 and 1202 displayed in natural language text display form concerning findings (image findings) and two entries 1203 and 1204 displayed in natural language text display form concerning diagnosis (imaging diagnosis). The identification information (ID) of the entry 1201 is "12345678-001", and the identification information (ID) of the entry 1202 is "12345678-005". The identification information (ID) of the entry 1203 is "12345678-002", and the identification information (ID) of the entry 1204 is "12345678-008".

Based on input information from the input device 14, the copy data generating unit 113 selects, for example, partial information and relation information (link) (temporary structured data) as copy targets from the structured document information (interpretation report or the like) displayed as shown in FIG. 8. Upon selecting the partial information and the relation information (link) as copy targets, the copy data generating unit 113 obtains the identification information (ID) of the partial information (entry) as a processing target from the storage unit 120. In addition, the copy data generating unit 113 obtains information indicating the type and contents of the selected partial information (entry) from the storage unit 120. Furthermore, the copy data generating unit 113 obtains information concerning the selected relation information (link) from the storage unit 120 based on the identification information of the partial information (entry).

The temporary structured data in FIG. 12A includes a structure in which links indicating cause-effect relations are set from the single entry 1201 to the plurality of entries 1203 and 1204, and a structure in which a link indicating an adversarial relation is set between the entries 1203 and 1204. With regard to these entries, the copy data generating unit 113 sets "link" elements in the text generation template. In addition, the copy data generating unit 113 sets, in the text generation template, information ("link" elements) for generating complementary data for explaining the relation information (links) as text data. In this manner, the copy data generating unit 113 generates a template (text generation template) for generating text data from the selected partial information and relation information (links).

FIG. 12B shows an example of the arrangement of the text generation template generated based on the selected partial information and links. An element 1205 includes entry elements of the entries 1201 and 1202 corresponding to the findings (image findings). Identification information for identifying the entries 1201 and 1202 is set to "entry id". Information describing a display format is set to "type". In the example in FIG. 12B, because natural language text display is selected, "plane" is set.

An element 1206 includes entry elements of the entries 1203 and 1204 corresponding to diagnosis (imaging diagnosis). Identification information for identifying the entries 1203 and 1204 is set to "entry id". Information describing a display format is set to "type". In the example in FIG. 12B, because natural language text display is selected, "plane" is set.

The pieces of identification information of three entries between which relation information (links) indicating cause-effect relations are set from the single entry 1201 to the plurality of entries 1203 and 1204 are set with comma delimiters at "link id" in a "link" element 1207. The pieces of identification information of entries between which relation information (link) indicating an adversarial relation is set between the plurality of entries 1203 and 1204 are set with comma delimiters at "link id1". The copy data generating unit 113 then generates data by converting the selected temporary structured data (partial information and relation information (links)) into text data by using the template (text generation template).

FIG. 12C shows an example of the text data generated by using the text generation template. A text portion 1208 is the text portion generated by expanding the element 1205 in the text generation template which corresponds to a finding (image finding). A text portion 1209 is the text portion generated by expanding the element 1206 in the text generation template which corresponds to diagnosis (imaging diagnosis).

A text portion 1210 is the text portion of the complementary data generated by expanding the "link" element 1207 (link element) in the text generation template. When partial information and relation information (link) selected as copy targets include relation information indicating a predetermined relation between the partial information (entries), the copy data generating unit 113 generates a text portion of complementary data like that described below. When, for example, relation information (links) indicating cause-effect relations is set from the single entry 1201 (finding 001) to the plurality of entries 1203 (diagnosis 002) and 1204 (diagnosis 008), the copy data generating unit 113 generates, as complementary data for explaining the relation information, text data indicating that diagnosis 002 and diagnosis 008 are derived from finding 001.

In addition, when relation information (link) indicating an adversarial relation is set between the entry 1203 (diagnosis 002) and the entry 1204 (diagnosis 008), the copy data generating unit 113 generates, as complementary data for explaining the relation information, text data indicating that diagnosis 002 contradicts diagnosis 008. The copy data generating unit 113 converts the selected partial information (entry) into text data by using the text generation template. In addition, the copy data generating unit 113 adds the complementary data generated by using the text generation template to the text data.

Referring back to the flowchart of FIG. 10, in step S1009, the copy data generating unit 113 generates copy data (FIGS. 11C and 12C) based on the text generation template (FIGS. 11B and 12B) generated from the temporary structured data. In step S1010, the copy data generating unit 113 saves the data generated in steps S1004, S1006, and S1009 in the copy buffer 121 (copy information storage unit), and terminates the processing.

Note that the method of generating a text generation template described in step S1008 is an example, and another method may be used. For example, a text generation template may be generated for each diagnosis entry from a group of entries directly linked to each diagnosis entry.

In addition, in this embodiment, a text generation template for generating copy text data is generated based on temporary structured data. However, a usable text generation template may be selected from a plurality of text generation templates prepared in advance. The copy data generating unit 113 can select a highly compatible text generation template as a usable text generation template based on the setting of a plurality of text generation templates prepared in advance and the comparison result obtained by comparing the contents of temporary structured data. In addition, based on the selected text generation template, the copy data generating unit 113 can also change the settings of the selected text generation template in accordance with the contents of the temporary structured data. In this case, the copy data generating unit 113 may manage text generation templates in association with the display formats of entry contents and the types of relation information (links), and specify a text generation template in accordance with designated conditions.

The copy data generating unit 113 decides the arrangement of partial information in copy information based on partial information and relation information selected as copy targets. For example, the copy data generating unit 113 decides the arrangement of partial information in a text generation template for generating text data to be pasted at a paste destination based on selected partial information and relation information. Based on the partial information (entries) and relation information obtained from the storage unit 120, the copy data generating unit 113 decides the arrangement of the partial information (entries) in the text generation template. The copy data generating unit 113 can then generate data by converting the format of partial information and relation information by using the text generation template whose arrangement has been decided.

In addition, based on the display state of partial information selected as a copy target, the copy data generating unit 113 decides the display format of the partial information in the copy information. For example, the copy data generating unit 113 decides the display format of partial information in a template for generating text data pasted at a paste destination. The copy data generating unit 113 can then generate data by converting the selected partial information based on the decided display format.

Furthermore, the copy data generating unit 113 decides at least one of the arrangement of partial information in copy information based on the partial information and relation information selected as copy targets and the display format of the partial information in the copy information based on the display state of the selected partial information. For example, the copy data generating unit 113 decides at least one of the arrangement of partial information in a template for generating the text data to be pasted at a paste destination and the display format of the partial information in the template based on the display state of the partial information. The copy data generating unit 113 then can generate data by converting the selected partial information and links based on the decision.

This embodiment has exemplified the arrangement configured to save generated data in the copy buffer 121 (copy information storage unit) after the generation of text data. However, the generated text generation template may be saved in the copy buffer 121 without any change. In this case, a system that pastes data or another type of medical information processing apparatus may read out a text generation template saved in the copy buffer 121, interpret the text generation template, and generate text data.

In addition, in this embodiment, the entry table 101 shown in FIG. 4A saves, as the contents of partial information (entry), both a plain text and structured data. However, the entry table 101 may save only one of them. When the contents of an entry are to be displayed on a window or converted into text data, the contents of the entry may be converted into a designated format based on the contents saved in the entry table 101. According to this embodiment, it is possible to save document information without any omission.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-188755, filed Sep. 27, 2016, which is hereby incorporated by reference herein in its entirety.

What is claimed is:

1. A medical information processing apparatus which processes structured document information including partial medical information obtained by classifying information concerning imaging diagnosis, the apparatus comprising:
    a memory storing a program; and
    one or more processors which, by executing the program, function as:
    a storage unit configured to store relation information indicating predefined relationships that define one or more relations between a number of pieces of partial medical information in the structured document information;
    a selection unit configured to select, based on a user input, a plurality of pieces of partial medical information, as copy targets, from the structured document information which is being displayed;
    a specifying unit configured to specify a relationship from the predefined relationships that was defined between the selected plurality of pieces of partial medical information using the storage unit, wherein the specified relationship and the selected plurality of pieces of partial medical information are the copy targets, selected by the selection unit; and
    a generating unit configured to generate first text data at a paste destination by copying the copy targets using the selected plurality of pieces of partial medical information,
    wherein the generating unit generates second text data at the paste destination by converting, to a text, relation information corresponding to the relationship specified by the specifying unit, in a case that the specifying unit specifies the relationship between the selected plurality of pieces of partial medical information, and
    wherein the relation information includes one or more of cause-effect relation medical information, adversarial relation medical information, and time-series relation medical information.

2. The apparatus according to claim 1, wherein the specifying unit determines a format of data configured to be processed at the paste destination at which copy information is pasted, and
    the specifying unit configured to generate a template for generating the first text data and the second text data from the plurality of pieces of partial medical information and the relation information, based on the determination result, when the first text data and the second text data are compatible at the paste destination.

3. The apparatus according to claim 2, wherein the storage unit is configured to hold identification information for specifying the plurality of pieces of partial medical information, information indicating a type and contents of the plurality of pieces of partial medical information, and the relation information,
    wherein the specifying unit generates the template by obtaining the plurality of pieces of partial medical information selected by the selection unit and the relation information, from the storage unit.

4. The apparatus according to claim 3, wherein the specifying unit decides an arrangement of the plurality of pieces of partial medical information in the template based on the plurality of pieces of partial medical information and the relation information obtained from the storage unit.

5. The apparatus according to claim 3, wherein the specifying unit selects a display format of the plurality of pieces of partial medical information in the template based on a display state of the plurality of pieces of partial medical information.

6. The apparatus according to claim 5, wherein the specifying unit selects, as the display format, one of display formats for natural language text display of the plurality of pieces of partial medical information and for display with attribute information concerning the imaging diagnosis being associated with information indicating values corresponding to the attribute information.

7. The apparatus according to claim 2, wherein when the plurality of pieces of partial medical information and the relation information include relation information indicating a predetermined relation between the pieces of partial medical information, the specifying unit sets, in the template, information for generating complementary data for explaining the relation information as the second text data.

8. The apparatus according to claim 7, wherein the generating unit generates data by converting the plurality of pieces of partial medical information into the first text data by using the template.

9. The apparatus according to claim 7, wherein the generating unit adds the complementary data generated by using the template to the second text data.

10. The apparatus according to claim 7, wherein the relation information includes information indicating a time-series relation between a plurality of pieces of partial medical information, information indicating a cause-effect relation set from one piece of partial medical information to a plurality of pieces of partial medical information, and information indicating an adversarial relation set between a plurality of pieces of partial medical information.

11. The apparatus according to claim 2, wherein when the determination result indicates that structured data is compatible at the paste destination, the generating unit generates the first text data and the second text data by converting the plurality of pieces of partial medical information and the relation information into structured data configured to be processed at the paste destination.

12. The apparatus according to claim 2, when the determination result indicates that image data is compatible at the paste destination, the generating unit generates the first text data and the second text data by converting the plurality of pieces of partial medical information and the relation information into image data configured to be processed at the paste destination.

13. The apparatus according to claim 1, wherein the plurality of pieces of partial medical information include a finding and a diagnosis, and in a case where the relation information indicating a cause-effect relation from the finding to the diagnosis is set, the generation unit generates the second text data indicating the diagnosis derived from the finding.

14. The apparatus according to claim 1, wherein the plurality of pieces of partial medical information include a first diagnosis and a second diagnosis, and in a case where the relation information indicating an adversarial relation between the first diagnosis and the second diagnosis is set, the generation unit generates the second text data indicating the adversarial relation between the first diagnosis and the second diagnosis.

15. A medical information processing apparatus which processes structured document information including partial medical information obtained by classifying information concerning imaging diagnosis, the apparatus comprising:
    a memory storing a program; and
    one or more processors which, by executing the program, function as:
    a storage unit configured to store relation information indicating predefined relationships that define one or more relations between a number of pieces of partial medical information in the structured document information;
    a selection unit configured to select, based on a user input, a plurality of pieces of partial medical information, as a copy target, from the structured document information which is being displayed;
    a specifying unit configured to specify a relationship from the predefined relationships that was defined between the selected plurality of pieces of partial medical information using the storage unit and a display format of the plurality of pieces of partial medical information in copy information based on a display state of the plurality of pieces of partial medical information, wherein the specified relationship and the selected plurality of pieces of partial medical information are the copy targets, selected by the selection unit; and
    a generating unit configured to generate first text data at a paste destination by copying the copy targets using the selected plurality of pieces of partial medical information based on the specified display format,
    wherein the generating unit generates second text data at the paste destination by converting, to a text, relation information corresponding to the relationship specified by the specifying unit, in a case that the specifying unit specifies the relationship between the selected plurality of pieces of partial medical information, and
    wherein the relation information includes one or more of cause-effect relation medical information, adversarial relation medical information, and time-series relation medical information.

16. A medical information processing apparatus which processes structured document information including partial medical information obtained by classifying information concerning imaging diagnosis, the apparatus comprising:
    a memory storing a program; and
    one or more processors which, by executing the program, function as:
    a storage unit configured to store relation information indicating predefined relationships that define one or more relations between a number of pieces of partial medical information in the structured document information;
    a selection unit configured to select, based on a user input, a plurality of pieces of partial medical information, as copy targets, from the structured document information which is being displayed;
    a specifying unit configured to specify an arrangement of the plurality of pieces of partial medical information in copy information based on the plurality of pieces of partial medical information selected by the selection unit and a relationship from the predefined relationships that was defined between the selected plurality of pieces of partial medical information using the storage unit, wherein the specified relationship and the selected plurality of pieces of partial medical information are the copy targets, selected by the selection unit; and
    a generating unit configured to generate first text data at a paste destination by copying the copy targets using the selected plurality of pieces of partial medical information based on the specified arrangement,
    wherein the generating unit generates second text data at the paste destination by converting, to a text, relation information corresponding to the relationship specified by the specifying unit, in a case that the specifying unit specifies the relationship between the selected plurality of pieces of partial medical information, and
    wherein the relation information includes one or more of cause-effect relation medical information, adversarial relation medical information, and time-series relation medical information.

17. A medical information processing apparatus which processes structured document information including partial medical information obtained by classifying information concerning imaging diagnosis, the apparatus comprising:
    a memory storing a program; and
    one or more processors which, by executing the program, function as:
    a storage unit configured to store relation information indicating predefined relationships that define one or more relations between a number of pieces of partial medical information in the structured document information;
    a selection unit configured to select, based on a user input, a plurality of pieces of partial medical information, as copy targets, from the displayed structured document information;
    a specifying unit configured to specify a data format which is configured to be processed at a paste destination at which the plurality of pieces of partial medical information selected by the selection unit and a relationship from the predefined relationships that was defined between the selected plurality of pieces of partial medical information using the storage unit, wherein the specified relationship and the selected plurality of pieces of partial medical information are pasted; and
    a generating unit configured to generate first text data at a paste destination by copying the copy targets using the selected plurality of pieces of partial medical information based on the specified data format, wherein the generating unit generates second text data at the paste destination by converting, to a text, relation information corresponding to the relationship between the selected plurality of pieces of partial medical information, and wherein the relation information includes one or more of cause-effect relation medical information, adversarial relation medical information, and time-series relation medical information.

18. A medical information processing system comprising a medical information processing apparatus which processes structured document information including partial medical information obtained by classifying information concerning imaging diagnosis, the apparatus comprising:

a memory storing a program; and
one or more processors which, by executing the program, function as:
a storage unit configured to store relation information indicating predefined relationships that define one or more relations between a number of pieces of partial medical information in the structured document information;
a selection unit configured to select, based on a user input, a plurality of pieces of partial medical information, as copy targets, from the displayed structured document information;
a specifying unit configured to specify a relationship from the predefined relationships that was defined between the selected plurality of pieces of partial medical information using the storage unit, wherein the specified relationship and the selected plurality of pieces of partial medical information are the copy targets, selected by the selection unit; and
a generating unit configured to generate first text data at a paste destination by copying the copy targets using the selected plurality of pieces of partial medical information, wherein the generating unit generates second text data at the paste destination by converting, to a text, the relation information corresponding to the relationship specified by the specifying unit, in a case that the specifying unit specifies the relationship between the selected plurality of pieces of partial medical information, and wherein the relation information includes one or more of cause-effect relation medical information, adversarial relation medical information, and time-series relation medical information.

19. A medical information processing method in a medical information processing apparatus which processes structured document information including partial medical information obtained by classifying information concerning imaging diagnosis, the method comprising:

storing relation information indicating predefined relationships that define one or more relations between a number of pieces of partial medical information in the structured document information;
selecting, based on a user input, a plurality of pieces of partial medical information, as copy targets, from the displayed structured document information;
specifying a relationship from the predefined relationships that was defined between the selected plurality of pieces of partial medical information, wherein the specified relationship and the selected plurality of pieces of partial medical information are the copy targets, selected in the selecting;
generating first text data at a paste destination by copying the copy targets using the selected plurality of pieces of partial medical information; and
generating second text data at the paste destination by converting, to a text, relation information corresponding to the relationship specified in the specifying, in a case that in the specifying, the relationship between the selected plurality of pieces of partial medical information is specified, wherein the relation information includes one or more of cause-effect relation medical information, adversarial relation medical information, and time-series relation medical information.

20. A non-transitory computer-readable storage medium storing a program for causing a computer to execute steps in a medical information processing method in a medical information processing apparatus which processes structured document information including of partial medical information obtained by classifying information concerning imaging diagnosis, the method comprising:

storing relation information indicating predefined relationships that define one or more relations between a number of pieces of partial medical information in the structured document information;
selecting, based on a user input, a plurality of pieces of partial medical information, as copy targets, from the displayed structured document information;
specifying a relationship from the predefined relationships that was defined between the selected plurality of pieces of partial medical information, wherein the specified relationship and the selected plurality of pieces of partial medical information are the copy targets, selected in the selecting;
generating first text data at a paste destination by copying the copy targets using the selected plurality of pieces of partial medical information; and
generating second text data at the paste destination by converting, to a text, relation information corresponding to the relationship specified in the specifying, in a case that in the specifying, the relationship between the selected plurality of pieces of partial medical information is specified, wherein the relation information includes one or more of cause-effect relation medical information, adversarial relation medical information, and time-series relation medical information.

21. A medical information processing apparatus which processes structured document information including partial medical information obtained by classifying information concerning imaging diagnosis, the apparatus comprising:

a memory storing a program; and
one or more processors which, by executing the program, function as:
a storage unit configured to store relation information indicating predefined relationships that define one or more relations between a number of pieces of partial medical information in the structured document information;
a selection unit configured to select, based on a user input, a plurality of pieces of partial medical information, as copy targets, from the structured document information which is being displayed;
a specifying unit configured to specify a relationship from the predefined relationships that was defined between the selected plurality of pieces of partial medical information using the storage unit, wherein the specified relationship and the selected plurality of pieces of partial medical information are the copy targets, selected by the selection unit and specify a format to be processed at a paste destination at which the copy targets are pasted; and a generating unit configured to generate first text data at the paste destination by copying the copy targets using the selected plurality of pieces of partial medical information, in a case that the copy targets are compatible with the format at the paste destination, wherein the generating unit generates second text data at the paste destination by converting, to a text, relation information corresponding to the relationship specified by the specifying unit, in a case that the specifying unit specifies the relationship between the selected plurality of pieces of partial medical information, and wherein the relation information includes one or more of cause-effect relation medical information, adversarial relation medical information, and time-series relation medical information.

\* \* \* \* \*